United States Patent [19]

Roby

[11] Patent Number: 5,696,285
[45] Date of Patent: Dec. 9, 1997

[54] PRODUCTION OF TEREPHTHALIC ACID WITH EXCELLENT OPTICAL PROPERTIES THROUGH THE USE OF PURE OR NEARLY PURE OXYGEN AS THE OXIDANT IN P-XYLENE OXIDATION

[75] Inventor: Anne Katherine Roby, Golden's Bridge, N.Y.

[73] Assignee: Praxair Technology, Inc., Danbury, Conn.

[21] Appl. No.: 586,022

[22] Filed: Dec. 29, 1995

[51] Int. Cl.$^6$ .................................................. C07C 51/16
[52] U.S. Cl. .................................................. 562/416
[58] Field of Search .................................................. 562/416

[56] References Cited

U.S. PATENT DOCUMENTS

| | | | |
|---|---|---|---|
| 2,833,816 | 5/1958 | Saffer et al. | 360/524 |
| 3,064,044 | 11/1962 | Baldwin | 260/524 |
| 3,089,906 | 5/1963 | Saffer et al. | 260/524 |
| 3,089,907 | 5/1963 | Saffer et al. | 260/524 |
| 3,092,658 | 6/1963 | Baldwin et al. | 260/524 |
| 4,769,487 | 9/1988 | Hundley et al. | 562/413 |
| 4,835,307 | 5/1989 | Lindahl et al. | 562/413 |
| 4,900,480 | 2/1990 | Litz et al. | 261/36.1 |
| 5,081,290 | 1/1992 | Partenheimer et al. | 562/416 |
| 5,099,064 | 3/1992 | Huber, Jr. et al. | 562/414 |
| 5,371,283 | 12/1994 | Kingsley et al. | 562/416 |
| 5,523,474 | 6/1996 | Kingsley | 562/416 |

FOREIGN PATENT DOCUMENTS 6-321855  11/1994  Japan.

OTHER PUBLICATIONS

Walt Partenheimer, "A Chemical Model for the Amoco MC Oxygenation Process to Produce Terephthalic Acid" *Chem. Ind. (Dekker)* 40 (*Catal. Org React*) 1990, pp. 321–346.

Pavagada Raghavendrachar et al, "Kinetics and Catalysis", *Ind.Eng.Chem Res.* 1992, 31, 453–462.

Roffia et al, "Byproduct Identification in the Terephthalic Acid Production Process and Possible Mechanisms of Their Formation", *Ind. Eng. Chem. Prod. Res. Dev.*, 1984, 23, 629–634.

Landau et al, "Development of M–C Process", *Chemical Engineering Progress* (vol. 64, No. 10).

*Primary Examiner*—Michael L. Shippen
*Attorney, Agent, or Firm*—Robert J. Follett

[57] ABSTRACT

The production of terephthalic acid by the oxidation of p-xylene is carried out in such a manner that the oxygen concentration in the liquid phase is maximized through the use of pure or nearly pure oxygen, while simultaneously the hydrocarbon feed concentration is minimized through rapid dilution with the reactor contents.

14 Claims, 2 Drawing Sheets

5,696,285

PRODUCTION OF TEREPHTHALIC ACID WITH EXCELLENT OPTICAL PROPERTIES THROUGH THE USE OF PURE OR NEARLY PURE OXYGEN AS THE OXIDANT IN P-XYLENE OXIDATION

FIELD OF THE INVENTION

This invention relates to a method for producing terephthalic acid (TA) and more particularly to a method for producing TA having improved optical properties.

BACKGROUND

Terephthalic acid is produced by the oxidation of p-xylene. The oxidation proceeds through a complex reaction path wherein several intermediates in the reaction exist in appreciable concentrations. These intermediates may react with each other to form undesirable, high molecular weight, colored by-products which are very stable. These by-products include, but are not limited to, fluorenones, benzophenones, diphenyls, anthraquinones and their derivatives. The presence of these by-products lowers the value of the TA product since coloring agents or optical brighteners must then be added to the polyester made from the TA.

A typical air based process for producing TA is described in U.S. Pat. No. 3,089,906 and more recently in U.S. Pat. Nos. 5,081,290 and 5,371,283. In this process liquid p-xylene is fed into a stirred tank reactor. A monobasic aliphatic acid such as acetic acid is used as a solvent. The ratio of solvent to reactant is typically two to six volumes of solvent per volume of reactant (2:1 to 6:1). The reaction is catalyzed with a heavy metal or mixture of heavy metals, most commonly cobalt and manganese in the form of acetate salts.

Bromine is used as a promoter and is typically in the form of bromic acid. The reactor is maintained at an operating temperature between 170° C. and 225° C. The operating pressure is such that a liquid is maintained in the reaction zone, approximately between 70 and 350 psig. Compressed air is sparged into the bottom of the reactor. Oxygen from the air dissolves into the liquid phase and reacts with p-xylene to produce TA. Intermediate oxidation products and by-products are formed in quantities which depend upon reaction conditions. At a residence time of one hour, the conversion of p-xylene is typically above 99% and yield to TA is typically greater than 95%.

Feed air must be compressed to a pressure somewhat above the reactor operating pressure before it is blown into the reactor through a pipe or other submerged sparger. As the bubbles are dispersed and circulated throughout the liquid phase by an agitator, the oxygen concentration in the bubbles decreases as the oxygen dissolves and reacts. The bubbles disengage from the liquid phase and collect in the top of the reactor to form a continuous gas phase. This waste gas must be vented in order to make room for fresh air feed and to maintain adequate gas hold-up to promote oxygen transfer from the gas to the liquid phase.

To avoid the possibility of fire or explosion, the oxygen concentration in the gas space at the top of the reactor must be maintained below the flammable limit. For practical purposes, the oxygen concentration must be maintained at less than 8–9% by volume as taught in U.S. Pat. No. 3,092,658. More typically, the oxygen concentration in the gas space is maintained below 5% by volume to provide a safe margin below the flammable limit. Thus in a well-mixed, stirred tank reactor, the average concentration of oxygen bubbles must be below 5% in order to insure that the average concentration of oxygen in the gas which collects in the headspace is nonflammable.

The oxygen concentration in the gas space is a function of the rate at which air is fed into the reactor and the rate of consumption of oxygen from the air by reaction. The rate of reaction and, therefore, the TA production rate per unit of reactor volume, increases with temperature, pressure, oxygen concentration in the liquid phase, p-xylene concentration, promoter concentration and catalyst concentration. Since the concentration of dissolved oxygen in the liquid phase and, hence, the reaction rate of oxygen is proportional to the oxygen concentration in the gas phase, for a given set of reaction conditions, the 5% oxygen restriction effectively limits the oxygen reaction rate.

Some practitioners of the art have attempted to minimize the formation of high molecular weight by-products by adjusting the air flow rate through the reactor, and therein, for a given hydrocarbon feed rate and reaction conditions, the oxygen concentration in the vent stream as disclosed in U.S. Pat. No. 4,835,307. This method effectively increases the average oxygen concentration in the liquid. However, because of the flammability hazard, the range through which the air flow rate can be adjusted is limited, since the maximum vent oxygen concentration must be maintained at less than 8–9%.

Another method which has been suggested to minimize areas of oxygen deficiency is discussed by Huber and Zeitlin in U.S. Pat. No. 5,099,064. In this method the concentration of reactant is artificially decreased from approximately 25% to 7% at the feed inlet to the reactor. The authors discuss that the "entrance" effect, i.e. the effect of having a region in the reactor where the hydrocarbon concentration is high relative to the available oxygen, can increase the generation of high molecular weight by-products. The authors claim that by minimizing the concentration of hydrocarbon relative to oxygen, the presence of color-body generation can be minimized. The process disclosed to accomplish this goal requires combining a refluxed condensate portion of the vaporized reaction mixture with the oxidation reactor liquid feed stream upstream from the oxidation reactor to produce a reflux-containing liquid feed mixture which is at a temperature below the reactor contents' temperature. This is a complicated procedure which requires additional apparatus and process steps.

As the production of TA is a highly significant commercial operation, there is a genuine need in the art for an improved TA process. In particular, there is a need to minimize the generation of intermediate high molecular weight colored impurities which harm the optical qualities of the final product.

OBJECTS OF THE INVENTION

It is an object of the invention, therefore to provide an improved process for the production of terephthalic acid.

It is another object of the invention to provide an improved oxygen based TA production process.

It is a further object of the invention to provide a process for TA production which yields TA having superior optical properties.

With these and further objects in mind, the invention is hereinafter described in detail, the novel features thereof being particularly pointed out in the appended Claims.

SUMMARY OF THE INVENTION

The production of terephthalic acid by the oxidation of p-xylene is carried out in such a manner that the oxygen concentration in the liquid phase is maximized through the use of pure or nearly pure oxygen (by pure or nearly pure we mean gas having at least 75 vol. % oxygen) while simultaneously the hydrocarbon feed concentration is minimized through rapid dilution with the reactor contents.

An especially preferred process for making terephthalic acid comprises the steps of:

a) providing a body of liquid contained within an oxidation reactor vessel, said body of liquid comprising an organic solvent, catalyst and a bromine initiator;

b) maintaining said body of liquid in a recirculating flow pattern by impeller means positioned therein;

c) injecting p-xylene reactant directly into said recirculating portion of the body of liquid at a reactant injection point or points of highest turbulence within a turbulent flow field produced by said impeller means so as to rapidly disperse the reactant into said body of liquid;

d) injecting pure or nearly pure oxygen into said body of liquid at a point of highest shear, which is directly adjacent to, and produced by said impeller means, so as to rapidly disperse oxygen in the liquid as small bubbles for rapid consumption upon injection into the liquid;

e) maintaining the oxygen-p-xylene mixture in the reactor vessel at a pressure of 90–150 psig, and a temperature between 170° C. and 190° C., for a residence time of about 60 minutes;

f) recovering terephthalic acid product having essentially no colored impurities directly from the oxidation reactor vessel.

It should be noted that the above procedure may be carried out with any oxidizeable aromatic alkyl.

BRIEF DESCRIPTION OF THE DRAWINGS

Other objects, features and advantages will occur to those skilled in the art from the following description of the preferred embodiments and the accompanying drawings, in which.

DETAILED DESCRIPTION OF THE INVENTION

We have observed that the aforementioned colored by-products are formed at an increased rate in regions of the reactor which are oxygen deficient. Accordingly, the objects of the invention are accomplished by carrying out the desired terephthalic acid production, using pure or nearly pure oxygen in place of air. Since the concentration of dissolved oxygen in the liquid phase is proportional to the oxygen concentration in the gas phase, the use of pure or nearly pure oxygen substantially increases the liquid phase oxygen concentration.

Further, the reactive components are added to the reactor in such a manner so as to maximize the availability of oxygen in the reactor, and to minimize the hydrocarbon concentration by rapid dilution. This prevents the formation of colored impurities which result from the coupling of reactive intermediates.

Finally, we have discovered that by combining the above conditions with specific temperature, pressure and flow rate parameters, essentially no high-molecular weight colored by-products are produced such that the resultant terephthalic acid has superior optical properties as compared to current industry standards.

In a preferred embodiment, the reaction takes place in a Liquid Oxidation Reactor (LOR) as described in U.S. Pat. No. 4,900,480, the teachings of which are herein incorporated by reference. Further references to an LOR are to the LOR of this patent.

In a particularly preferred embodiment, the TA production reaction takes place in a manner which enables evaporative cooling to be employed, particularly through the advantageous use of a modified LOR process and system, hereinafter referred to as an evaporatively cooled LOR.

Figure 1:
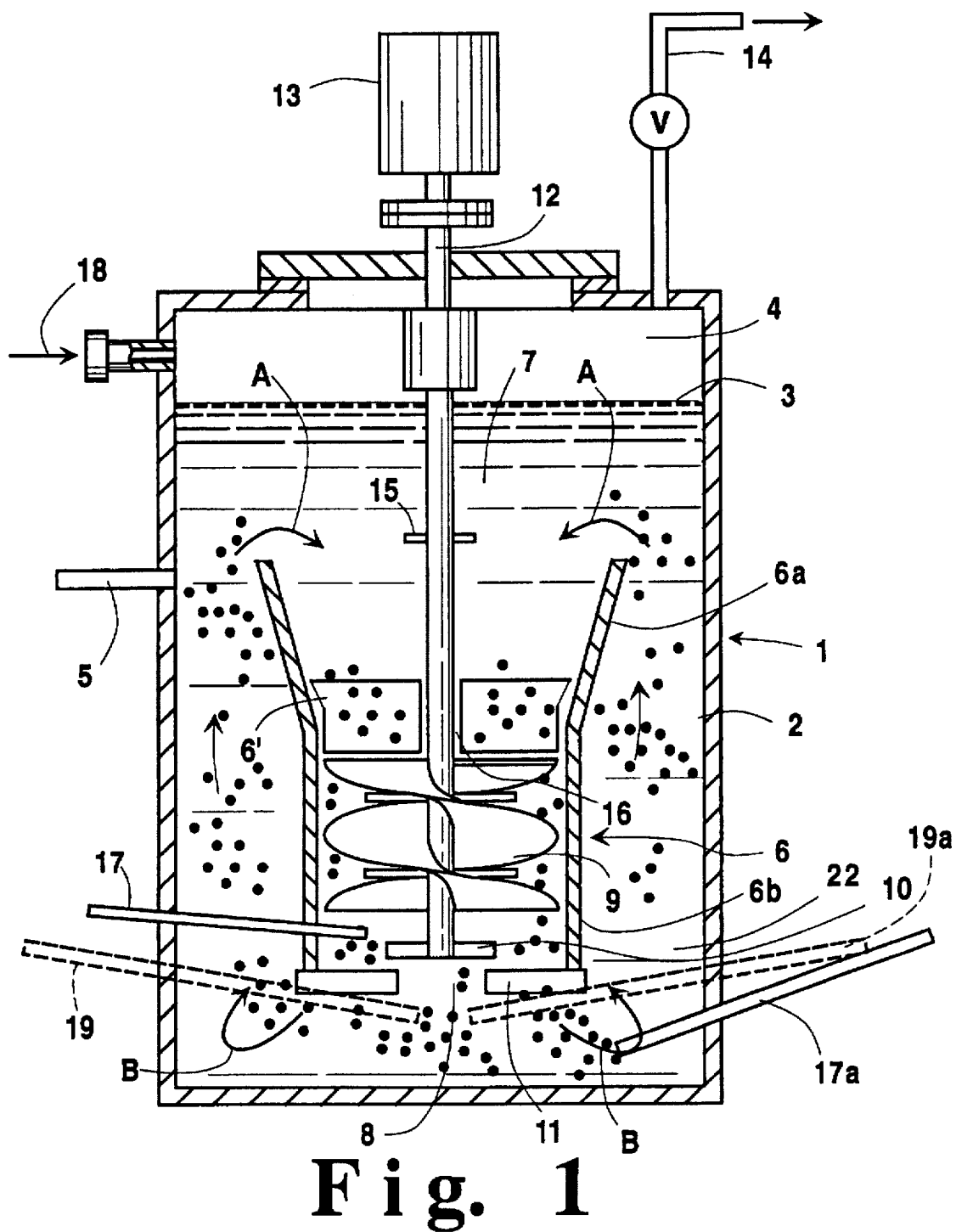
FIG. 1 is a schematic side elevational view of an oxygen-p-xylene reactor vessel which is used in the invention.

In the above preferred embodiments, oxygen is fed into the LOR, through feed 17, at a point which referring to FIG. 1, is between the helical impeller means 9 and the radial flow impeller means 10. Simultaneously, the reactant hydrocarbon is fed into the reactor, through feed 17a, at the point therein of highest turbulence, which is indicated by letter B in FIG. 1.

In comparison examples, oxygen and reactant were fed at the exit to the draft tube, as shown by feeds 19 and 19a, respectively. It will be appreciated that this feed area has significantly less turbulence than the feed areas of the invention. As the comparative data will show, this has a significant impact on the purity of the terephthalic acid product recovered directly from the reactor.

In an alternative embodiment in which a conventional reactor is used, pure or nearly pure oxygen is fed into the reactor at the point of highest shear, which is adjacent to a radial flow impeller means, while the hydrocarbon is simultaneously dispersed in the area of highest turbulence within the circulation flow pattern therein.

While the TA product is obtained in the solid phase, the use of the evaporative LOR avoids the practical operating problems associated with the common use of direct cooling heat exchange surfaces for removing the heat of the oxidation reaction that result from TA and other solids precipitation on the heat transfer surfaces of cooling coils and the like. Thus, the safe and efficient use of pure or nearly pure oxygen for the p-xylene oxidation reaction can conveniently be carried out using evaporative cooling to remove the heat of reaction generated during the oxidation reaction.

The LOR process and system, as employed in the practice of the invention, enables pure or nearly pure oxygen to be used instead of air, while obviating the potential for fire or explosion, under desirable operating conditions serving to minimize the amount of undesired byproducts present in the terephthalic acid product. In addition, the amount of vent gas to be treated is minimized. Furthermore, the invention can be carried out at lower operating temperatures and/or pressures than are typically employed in conventional air based processes, while achieving equivalent TA production. Undesired reactions that consume solvent and reactant, and produce byproduct gases, are suppressed at the modest operating temperature conditions conveniently used in the practice of the invention.

In the LOR process and system as described in the Litz et al. patent, U.S. Pat. No. 4,900,480, oxygen and the body of liquid are mixed and recirculated without appreciable loss of oxygen to the overhead gas phase. In the practice of the FIG. 1 embodiment of this invention, oxygen is largely consumed in the first pass through the downward pumping helical impeller/draft tube combination positioned within the reactor vessel, and within the roll cells referred to below. As a result thereof and of the modified system configuration employed in desirable embodiments of the invention, the recirculation of oxygen and other gas bubbles through the draft tube is minimized.

One of the important advantages of the LOR approach of the invention is that the gas-liquid reaction mixture is pumped from the draft tube positioned near the bottom of the reactor vessel at high velocities, thereby forming a jet that entrains surrounding fluid outside the draft tube and that impacts the bottom of the reactor vessel, thereby setting up roll cells in said reaction mixture in the bottom portion of the reactor. These roll cells essentially trap the dispersed gas phase until it is either completely consumed or coalesces to a critical bubble diameter having sufficient buoyancy to rise through the liquid and escape. This pattern of fluid dynamics yields very high oxygen use efficiency even in a single pass through the impeller positioned in the draft tube.

FIG. 1 of the drawings illustrates a modified LOR system suitable for use in accordance with the invention for the oxidation of p-xylene with pure or nearly pure oxygen, using evaporative cooling of the reaction mixture. In this embodiment, reactor vessel 1 has a body of organic liquid 2 therein, with an optional gas-liquid interface 3 and an optional overhead gas phase 4. In this regard it is noted that the reactor may be run in a "liquid full" process wherein the gas phase is not separated from the liquid until they are outside the reactor.

Returning to the discussion of the FIG. 1 embodiment, product liquid is removed from reactor vessel 1 through line 5. As in the LOR system of Litz et al., hollow draft tube 6 is typically centrally positioned within reactor vessel 1, with open end 7 at the top and open end 8 at the bottom thereof. Impeller means 9 are positioned within hollow draft tube 6. Such impeller means 9 are downward pumping helical impeller means adapted to facilitate the downward flow of liquid at high velocity from said body of liquid 2 in hollow draft tube 6, the formation of turbulent roll cells B, and upward flow of said liquid therefrom in the annulus between the side wall of the reactor vessel and the outside of hollow draft tube 6 above said roll cells B. Impeller means 9 commonly include radial flow impeller means 10 and, if desired, lower baffle means 11 to facilitate the desired recirculating flow of liquid in reactor vessel 1. A suitable drive shaft 12 that extends upward from reactor vessel 1 for connection to suitable driving means 13 used to operate impeller means 9.

Figure 2:
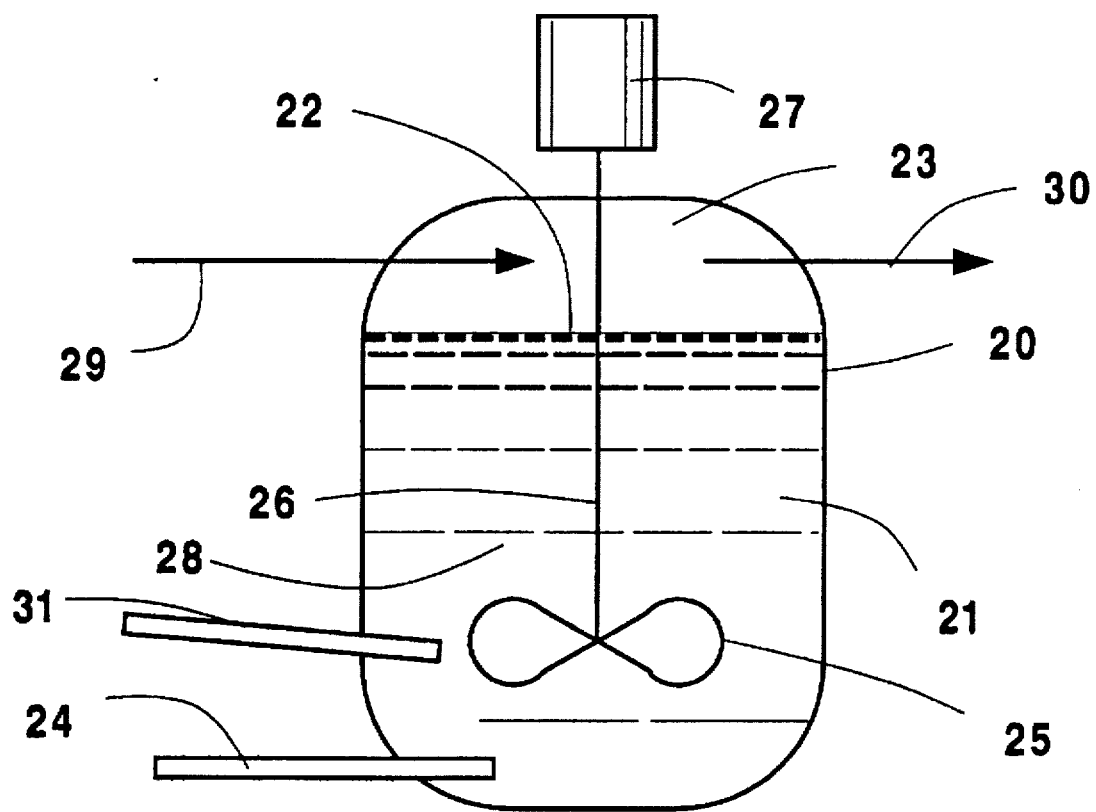
FIG. 2 is a schematic side elevational view of a conventional reactor design that can be employed in operations of the invention using pure or nearly pure oxygen for the oxidation of p-xylene.

In FIG. 2 of the Litz et al. patent referred to above, it will be noted that hollow draft chamber 29 optimally includes a conically flared portion 30a at the upper end thereof for purposes of facilitating the flow of a gas bubble-liquid mixture into the draft chamber for downward passage therein. In the modified LOR system of the invention, a conically flared portion is likewise positioned at the upper end of the hollow draft tube 6, but the configuration of said conically flared portion is quite different than that of Litz et al., and it is used for the opposite purpose of reducing the amount of gas bubbles drawn downward into hollow draft tube 6. Thus, vertically elongated, conically flared portion 6a of hollow draft tube 6 extends upward above the generally cylindrical bottom portion 6b thereof in which impeller means 9 is positioned. The increase in diameter at the top of said conically flared portion 6a serves to minimize the downward velocity of liquid flow pattern A across the top of said hollow draft tube 6, thereby appreciably reducing the portion of the gas bubbles rising in the reactor vessel outside said hollow draft tube 6 that are drawn down into impeller means 9 with the downward flow of reactant liquid in hollow draft tube 6. For this purpose, vertically elongated, conically flared upper portion 6a extends in vertical distance from about 0% to about 200%, preferably about 100% to about 150%, of the length of the bottom portion 6b of said hollow draft tube, in which impeller means 9 are positioned, and which is typically of cylindrical, non-tapered configuration. The diameter at the top of said draft tube, i.e., the enlarged diameter at the top of upper portion 6a, is appropriately sized to minimize the downward velocity of liquid across the top of the draft tube. While the dimensions of said upper portion 6a of draft tube 6 will be understood to vary depending on the overall circumstances of a given application, a clearance of from about 0.5 to about 4.0 times the diameter of the draft tube will typically pertain between said upper portion 6a and the walls of the reaction vessel. In some instances, the enlarged diameter of upper portion 6a will be from 1.5 to 3.0 times the diameter of hollow portion 6b. In particular embodiment's, the enlarged diameter at the top of upper portion 6a will be from about 40% to about 80% of the inside diameter or width of reactor vessel 1, preferably from about 50% to 60% thereof. The geometry and rotational speed of the impeller means are factors in determining the size of draft tube 6, and upper portion 6a thereof, for a particular application. The high velocity of the liquid pumped downward through the impeller means will typically be in the range of 5 to 20 ft./sec., such as to create the high turbulent rolls cells that trap undissolved oxygen and enhance the desired dissolution thereof. Baffle means 6' is also desirably positioned in said conically flared portion 6a of hollow draft tube 6 to facilitate the downward flow of liquid to impeller means 9.

As a result of the rapid consumption of feed oxygen upon injection into hollow draft tube 6, and the minimizing of the downward flow of liquid across the top of said draft tube, the modified LOR impeller/draft tube combination of the invention effectively reduces the amount of recirculated gas passing downward in the draft tube. The gas bubbles passing upward in liquid flow pattern B in the reaction vessel outside bottom portion 6b of the hollow draft tube comprise principally volatile organic chemicals (VOCs), reactant solvent, water vapor and by products, such as CO and $CO_2$, with only small amounts of undissolved oxygen being present therein. The evaporation of the volatile organic species provide the evaporative cooling needed to remove the heat of reaction of the desired organic chemical oxidation operation. It will be seen that the gas bubbles rising in reactor vessel 1, particularly in the vicinity of the top of upper portion 6a of hollow draft tube 6, and in the region above the draft tube to gas-liquid interface 3 contain very little, i.e. substantially no oxygen, so that the oxygen concentration in overhead gas phase 4 is readily maintained within the indicated limits to assure against the possibility of fire or explosion. The region of the body of liquid 2 near the top upper portion 6a of hollow draft tube 6 and in the portion of liquid body 2 above said upper portion 6a thus constitutes, in effect, a relatively quiescent zone of less turbulence analogous to that provided in the LOR process and system of the Litz et al. patent. It will be understood that gases are vented from overhead gas phase 4, through vent means 14, during the oxidation reaction process. For purposes of the invention, it should also be noted that the lower non-flared portion 6b of hollow draft tube 6 is desirably positioned in the lower half of reactor vessel 1, as shown in FIG. 1, preferably near the bottom of said vessel so as to provide impact between the gas bubble-liquid mixture being discharged from the bottom of reactor vessel 1 and the bottom of the reactor vessel.

In furtherance of the entirely different gas flow patterns desired in the practice of the invention visa-vis the gas-liquid mixing operation described in the Litz et al. patent, baffle means corresponding to guide baffle means 34, used in the Litz et al. system to direct a gas bubble-liquid mixture to the top of hollow draft chamber 29, are not employed in the practice of the invention. The invention does, however, employ a small horizontal baffle means, i.e. disc 15, positioned above the upper portion of the hollow draft tube 6a an around drive shaft 12 in the region above the impeller means. Such baffle means serve to preclude the ingestion of gas, by vortex action, from overhead gas phase 4 along said drive shaft 12.

As indicated above, the invention uses pure or nearly pure oxygen for the oxidation of p-xylene, with evaporative cooling being employed to remove the heat of reaction generated by the oxidation reaction. For this purpose, the mass transfer of oxygen from the gas phase to the liquid phase is substantially enhanced so as to increase the overall rate of reaction as compared to air based oxidation reactions. The practice of the invention enables a rapid rate of oxygen consumption to be achieved such that a very high oxygen use efficiency, i.e., at least 75% and preferably 90% or more, is obtained upon the first injection of pure or nearly pure oxygen directly into hollow draft tube 6 as herein described. Such oxygen utilization, coupled with the configuration of said hollow draft tube 6 as described above, minimizes the recirculation of gas bubbles through said draft tube 6, enables evaporative cooling to be advantageously employed, and precludes undesired cavitation in impeller means 9 that would impede or preclude the desired recirculation of liquid reactant, originally fed through injection line 17a, and the breaking up and rapid dispersion of oxygen as fine bubbles in the liquid reactant.

For purposes of the preferred evaporative cooling approach of the invention, the oxygen is added to reactor vessel 1 at a point of high turbulence within hollow draft tube 6 rather than elsewhere in the body of organic liquid 2. While oxygen addition can be made at any convenient point of high turbulence in said hollow draft tube 6, or just below it, such as, for example, through injection line 16 directly to lower portion 6b thereof immediately above impeller means 9, it is desirable and convenient to inject oxygen into the system, through injection line 17 to a point in said lower portion 6b below helical impeller means 9 and radial flow impeller means 10, such as flat blade turbines, if employed, or to a point in said lower portion 6b between helical impeller means 9 and said radial flow impeller means 10, if employed. It will be appreciated that these are points of high turbulence and that the injection of the oxygen at such a point of high turbulence is important to the desired rapid consumption of oxygen. The initially high concentration of oxygen in the gas phase at the point of injection serves to enhance the mass transfer rate of the oxygen into this region of the liquid reactant, which would be otherwise oxygen depleted in the liquid phase due to the rapid rate of the oxidation reaction.

In the practice of the FIG. 1 embodiment of the invention, it will be understood that nitrogen or other inert purge gas can be passed into overhead gas phase 4 through line 18 principally to inert the small amounts of unreacted oxygen that may escape into the overhead gas phase. Note that in the "liquid full" process, the purge gas is added to the gas stream outside the reactor vessel.

Returning to the FIG. 1 embodiment, it should be noted that the draft tube configuration is an excellent pump, which sets up the above-indicated roll cells that trap undissolved oxygen, which allows high oxygen efficiency to be achieved and limits the amount of nitrogen or other inert purge gas required in the overhead gas phase compared to the FIG. 2 embodiment discussed below. The roll cells form a very significant portion of the turbulent flow field produced by said impeller means.

In the TA production operation, a significant amount of organic material and water evaporate from the reaction mixture. The vent gases are desirably cooled, and the condensibles therefrom are returned to the reactor in preferred embodiments of the invention. A portion of the vent flow is desirably diverted for gas analysis of carbon dioxides and oxygen. The oxygen utilization efficiency observed in the practice of the invention for the reaction of p-xylene with oxygen is greater than about 95%. That is, less than about 5% of the oxygen that is fed to the reactor is vented unreacted.

The relative benefits due to the use of pure or nearly pure oxygen in accordance with the practice of the invention instead of air in the conventional process for the production of TA are observed over the range of suitable operating conditions, and the optimal operating conditions for the oxygen-based process of the invention are generally more favorable than those that pertain in the practice of the conventional air based process.

As indicated above, in less preferred embodiments, the use of oxygen in the oxidation of organic chemicals, e.g. hydrocarbons, can be carried out in conventional reactor vessels.

In FIG. 2 of the drawings, reactor vessel 20 containing a body of solvent, initiator and catalyst, with gas-liquid interface 22 and overhead gas phase 23, has oxygen injected therein through line 24. Impeller means 25, driven by drive shaft 26 and drive motor 27, is used to disperse the oxygen in the form of bubbles 28 in said body of liquid reactant 21. Simultaneously reactant is fed through line 31. Nitrogen or other inert vent gas is introduced into overhead gas phase 23 through line 29, and vent gas is withdrawn therefrom through line 30.

Under such conditions, many of the advantages observed with oxygen based processing, i.e., increased reaction rate, decreased vent flow, reduction in byproduct formation, are realized. Because the flow patterns are different in systems such as shown in FIG. 2, however, oxygen is not trapped in roll cells, such as those advantageously formed in the LOR embodiment of FIG. 1, and more of the undissolved oxygen escapes into the overhead gas phase. Therefore, the system of FIG. 2 is less oxygen efficient than the FIG. 1 embodiment and requires the use of more nitrogen or other inert gas for safety purposes. Thus, to avoid safety problems associated with dangerous concentrations of oxygen in overhead gas phase 23 in such reactor operations, a large amount of nitrogen or other inert vent gas must be passed to said overhead gas phase 23 to avoid safety problems associated with the presence of excess oxygen in said gas phase. The additional cost of such nitrogen or other gas could well render this embodiment uneconomical from a practical operating viewpoint.

Many of the advantages recited above for the practice of the preferred embodiment of the invention as illustrated in FIG. 1 would be realized in the practice of the less preferred FIG. 2 embodiment, i.e., increased reaction rate, decreased vent flow, reduction in byproduct formation. In addition to the large nitrogen or other inert gas flow to the overhead gas space, the oxygen utilization efficiency of the FIG. 2 embodiment is much lower than for the FIG. 1 embodiments of the invention, or for the embodiments of the Litz patent, because there is no provision for the recirculation of unreacted oxygen, i.e. in the roll cells of the FIG. 1 embodiment. Thus, more oxygen would be required, since more of the oxygen passed to the reactor would be vented unreacted. The additional amounts of oxygen and nitrogen required in the FIG. 2 approach, and the associated costs, render said FIG. 2 embodiment less desirable, and perhaps uneconomical, for various commercial applications of the TA production operation.

In the practice of the invention, a preferred solvent:reactant ratio is from about 1:1 to about 8:1 on a volume:volume basis. The preferred catalyst loadings should be within the following ranges: cobalt (400–700 ppm), manganese (800–1700 ppm), and bromine (500–1200 ppm). The total loading should be between 500–3000 ppm, and the Co:Mn ratio should be from 1:10 to 10:1. A preferred residence time for the liquid is about 60 minutes, though a time between 30 and 90 minutes is suitable. The operating temperature is generally between about 170° C. and about 190° C., preferably 180° C. to 190° C. The operating pressure is about 90–300 psig, preferably 100–125 psig, most preferably 115 psig. The preferred hydrocarbon reactant feed concentration varies between about 8.9% and about 14.2%. The preferred water feed varies between 5.3% and 10.5%. The oxidant should be pure or nearly pure oxygen.

Tables 1 and 2 set forth the reaction parameters and properties for examples illustrative of the invention (Runs 1–6) as well as comparison examples (Runs 7–9). All of the examples use the reactor system shown in FIG. 1, and differ only in that Runs 1–6 use and oxygen and reactant feed points 17 and 17a, respectively; whereas Runs 7–9 use oxygen and reactant feed points 19 and 19a, respectively. As noted above, the latter feed area has significantly less turbulence than the feed areas of the invention, and as such the hydrocarbon concentration is greater in the vicinity of the oxygen as compared to the practice of our invention.

Note that "PRES" is pressure; "P-XYL" is the amount of p-xylene in acetic acid solvent; "WATER" is the amount of water in acetic acid solvent. Co, Mn and Br are measured in ppm. The reaction time in the evaporative LOR was 60 minutes.

TABLE 1

| RUN | PRES (psig) | TEMP. (°C.) | CO | MN | BR | P-XYL | WATER |
| --- | --- | --- | --- | --- | --- | --- | --- |
| 1 | 115 | 189 | 420 | 1350 | 880 | 13.2% | 5.3% |
| 2 | 115 | 180 | 400 | 1420 | 1000 | 8.9% | 5.3% |
| 3 | 115 | 184 | 540 | 640 | 390 | 9.5% | 10.5% |
| 4 | 115 | 184 | 510 | 840 | 510 | 14.2% | 8.8% |
| 5 | 116 | 186 | 560 | 810 | 460 | 9.2% | 10.5% |
| 6 | 115 | 185 | 510 | 790 | 510 | 9.1% | 10.4% |
| 7 | 100 | 181 | 480 | 710 | 430 | 11.7% | 8.4% |
| 8 | 100 | 182 | 510 | 440 | 300 | 11.8% | 8.4% |
| 9 | 151 | 197 | 390 | 1300 | 1690 | 14.1% | 10.7% |

As indicated above, the properties obtained in these experiments are shown below in Table 2. These were obtained from TA product recovered directly from the reactor vessel. No additional washing or purification steps were required. "PTA" is p-toluic acid and "4-CBA" is 4-carboxybenzaldehyde.

Optical density was measured using a Perkin Elmer, Lamda 2, UV/VIS Spectrophotometer and following the procedures disclosed in U.S. Pat. No. 5,095,146, the contents of which are herein incorporated by reference. In our measurements the path length was 10 mm.

TABLE 2

| RUN | OD @ 340 nm | PTA | 4-CBA | TA |
| --- | --- | --- | --- | --- |
| 1 | 1.28 | 0.1% | 0.2% | 96.9% |
| 2 | 0.00 | 0.4% | 0.4% | 96.8% |
| 3 | 0.00 | 0.0% | 0.1% | 99.1% |
| 4 | 0.01 | 0.0% | 0.3% | 98.7% |
| 5 | 0.07 | 0.0% | 0.2% | 98.7% |
| 6 | 0.01 | No data | No data | No data |
| 7 | 3.51 | 0.1% | 0.8% | 96.5% |
| 8 | 3.83 | 0.1% | 1.1% | 96.6% |
| 9 | 16.40 | 0.1% | 0.6% | 95.6% |

As can be seen, the process of the invention yields TA having superior optical properties. Further, because high quality TA is obtained directly from the reactor vessel, without the requirement of additional purification steps, significant cost savings are also realized.

In comparison, when reactant is injected into a non-turbulent point in the reactor the optical density nearly triples, a result which was not expected. As such, there is clear evidence as to the criticality of the reactant injection point in the present invention.

It should be noted that the optimal operating conditions for a specific embodiment of the invention are largely determined by the economics applicable to that embodiment. As indicated above, an increase in operating temperature increases solvent loss and improves product quality.

Those skilled in the art will appreciate that various changes and modifications can be made in the details of the invention without departing from the scope thereof as recited in the appended claims. For example, a solvent other than acetic acid, e.g., a monobasic aliphatic acid containing two to six carbon atoms, could be employed. In addition, the above process is suitable for the oxidation of any other organic chemical whose oxidation produces a solid as a product or by-product. Such chemicals include, but are not limited to toluene, meta- and ortho-xylene and trimethylbenzenes. The resultant products include, but are not limited to benzoic acid, orthophthalic acid, isophthalic acid and benzenetricarboxylic acids. In addition to the production of TA, the production of isophthalic acid, trimellitic acid and 2,6-dicarboxynaphthalene are logical extrapolations of the technology. It should be noted that the use of the evaporative LOR is not required, or even preferred in the production of aromatic carboxylic acids that do not produce solid by-products. Examples of these carboxylic acids are trimellitic acid.

As seen from the illustrated embodiments, pure or nearly pure oxygen is injected directly into the recirculating portion of the body of liquid at an oxygen injection point or points near the impeller means. For purposes of this invention, a position near the impeller means is one within the turbulent flow field produced by the impeller means, including the impeller suction and discharge flow fields. The turbulent flow field also significantly includes the roll cells, i.e. roll cells B in FIG. 1, formed in the reactor vessel below the hollow draft tube and said impeller means.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A process for making an aromatic carboxylic acid, said process comprising the steps of:

a) providing a body of liquid contained within a reactor vessel, said body of liquid comprising an organic solvent, at least one catalyst selected from the group consisting of manganese and cobalt, and a bromine initiator;

b) maintaining said body of liquid in a recirculating flow pattern by impeller means positioned therein;

c) injecting an aromatic alkyl reactant directly into said recirculating portion of the body of liquid at a reactant injection point or points of highest turbulence within a turbulent flow field produced by said impeller means so as to rapidly disperse the reactant into said body of liquid;

d) injecting pure or nearly pure oxygen into said body of liquid at a point of highest shear which is directly adjacent to, and produced by said impeller means, so as to rapidly disperse oxygen in the liquid as small bubbles for rapid consumption upon injection into the liquid;

e) maintaining the oxygen-aromatic alkyl mixture in the reactor vessel at a pressure of 90–300 psig, and a temperature between 170° C. and 190° C., for a residence time of about 60 minutes;

f) recovering aromatic carboxylic acid product having essentially no colored impurities directly from the reactor.

2. The process of claim 1, wherein the aromatic carboxylic acid is terephthalic acid, trimellitic acid, isophthalic acid or 2,6-dicarboxynaphthalene.

3. The process of claim 1, wherein the aromatic alkyl is p-xylene and the aromatic carboxylic acid is terephthalic acid, wherein if the catalyst is cobalt it is present in an amount of 400–700 ppm, and if the catalyst is manganese it is present in an amount of 800–1700 ppm, and wherein the bromine initiator is HBr and is present in an amount of 500–1200 ppm.

4. The process of claim 1, wherein the solvent:reactant ratio is from about 1:1 to about 8:1 on a volume:volume basis.

5. The process of claim 1, wherein the reactor vessel is a liquid oxygen reactor.

6. The process of claim 1, wherein the reactor vessel is an evaporatively cooled liquid oxygen reactor.

7. The process of claim 1, wherein the reaction temperature is 180° C. to 190° C.

8. The process of claim 1, wherein the pressure is 100–125 psig.

9. The process of claim 1, wherein the pressure is 115 psig.

10. A process for making an aromatic carboxylic acid, said process comprising the steps of:

a) providing a body of liquid contained within a reactor vessel, said body of liquid comprising an organic solvent, at least one catalyst selected from the group consisting of manganese and cobalt, and a bromine initiator;

b) maintaining said body of liquid in a recirculating flow pattern by impeller means positioned therein;

c) injecting an aromatic alkyl reactant directly into said recirculating portion of the body of liquid at a reactant injection point or points of highest turbulence within a turbulent flow field produced by said impeller means so as to rapidly disperse the reactant into said body of liquid;

d) injecting pure or nearly pure oxygen into said body of liquid at a point of highest shear which is directly adjacent to, and produced by said impeller means, so as to rapidly disperse oxygen in the liquid as small bubbles for rapid consumption upon injection into the liquid;

e) maintaining the oxygen-aromatic alkyl mixture in the reactor vessel at a pressure of 90–300 psig, and a temperature between 170° C. and 190° C., for a residence time of about 60 minutes;

f) recovering aromatic carboxylic acid product having essentially no colored impurities directly from the reactor, wherein the aromatic alkyl is p-xylene, the aromatic carboxylic acid is terephthalic acid, and the reactor is a liquid oxygen reactor.

11. The process of claim 10, wherein the aromatic alkyl is p-xylene and the aromatic carboxylic acid is terephthalic acid, wherein if the catalyst is cobalt it is present in an amount of 400–700 ppm, and if the catalyst is manganese it is present in an amount of 800–1700 ppm, and wherein the bromine initiator is HBr and is present in an amount of 500–1200 ppm.

12. The process of claim 10, wherein the reactor is an evaporatively cooled liquid oxygen reactor.

13. The process of claim 11, wherein the reactor is an evaporatively cooled liquid oxygen reactor.

14. A process for making a terephthalic acid having an optical density, as measured at 340 nm, of less than or equal to 1.28, said process comprising the steps of:

a) providing a body of liquid contained within a reactor vessel, said body of liquid comprising an organic solvent, at least one catalyst selected from the group consisting of manganese and cobalt, and a bromine initiator;

b) maintaining said body of liquid in a recirculating flow pattern by impeller means positioned therein;

c) injecting an p-xylene reactant directly into said recirculating portion of the body of liquid at a reactant injection point or points of highest turbulence within a turbulent flow field produced by said impeller means so as to rapidly disperse the reactant into said body of liquid;

d) injecting pure or nearly pure oxygen into said body of liquid at a point of highest shear which is directly adjacent to, and produced by said impeller means, so as to rapidly disperse oxygen in the liquid as small bubbles for rapid consumption upon injection into the liquid;

e) maintaining the oxygen and p-xylene mixture in the reactor vessel at a pressure of 90–300 psig, and a temperature between 170° C. and 190° C., for a residence time of about 60 minutes;

f) recovering terephthalic acid product having an optical density, as measured at 340 nm, of less than or equal to 1.28 directly from the reactor.

* * * * *